US005635374A

United States Patent [19]

Kiefer et al.

[11] Patent Number: 5,635,374

[45] Date of Patent: Jun. 3, 1997

[54] BONE CALCIFICATION FACTOR AND RECOMBINANT PRODUCTION OF THE FACTOR NUCLEIC ACID ENCODING

[75] Inventors: Michael C. Kiefer, Clayton; Frank R. Masiarz, San Francisco; Philip J. Barr, Oakland, all of Calif.

[73] Assignee: Chiron Corporation, Emeryville, Calif.

[21] Appl. No.: 237,243

[22] Filed: May 4, 1994

Related U.S. Application Data

[63] Continuation of Ser. No. 890,362, May 22, 1992, abandoned, which is a continuation of Ser. No. 360,826, Jun. 2, 1989, abandoned.

[51] Int. Cl.[6] .......... C12N 15/18; C12N 15/81

[52] U.S. Cl. .......... 435/69.4; 435/69.8; 435/254.2; 435/320.1; 536/23.5; 536/23.51; 536/24.31

[58] Field of Search .......... 536/23.5, 23.51, 536/24.31; 435/69.4, 69.8, 254.2, 320.1

[56] References Cited

U.S. PATENT DOCUMENTS

| | | | |
|---|---|---|---|
| 4,294,753 | 10/1981 | Urist | 260/112 R |
| 4,394,370 | 7/1983 | Jefferies | 424/15 |
| 4,434,094 | 2/1984 | Seyedin et al. | 260/112 R |
| 4,455,256 | 6/1984 | Urist | 260/112 R |
| 4,526,909 | 7/1985 | Urist | 523/115 |
| 4,563,489 | 1/1986 | Urist | 524/21 |
| 4,596,574 | 6/1986 | Urist | 623/16 |
| 4,619,989 | 10/1986 | Urist | 530/417 |
| 4,627,982 | 12/1986 | Seyedin et al. | 424/95 |
| 4,761,471 | 8/1988 | Urist | 530/350 |
| 4,795,804 | 1/1989 | Urist | 530/350 |
| 4,804,744 | 2/1989 | Sen | 530/350 |
| 4,810,691 | 3/1989 | Seyedin et al. | 514/2 |

FOREIGN PATENT DOCUMENTS

| | | |
|---|---|---|
| 0 148 155 | 10/1985 | European Pat. Off. . |
| A-0196056 | 1/1986 | European Pat. Off. . |
| A-0212474 | 4/1987 | European Pat. Off. . |
| 0 289 314 | 7/1987 | European Pat. Off. . |
| 0 336 760 | 2/1988 | European Pat. Off. . |
| 2 164 042 | 4/1990 | United Kingdom . |
| WO 88/00205 | 1/1988 | WIPO . |
| WO-A-9003734 | 4/1990 | WIPO . |

OTHER PUBLICATIONS

Price et al., "Characteriztion of γ-carboxyglutamic acid-containing protein From Bone," Proc. Natl. Acad. Sci. USA (1976), 73:1447–1451.

Price et al., "Matrix Gla Protein, A New γ-carboxyglutamic Acid-Containing Protein which is Associated with the Organic Matrix of Bone," Biochem. Biophys. Res. Comm. (1983), 117:765–771.

Price et al., "Primary Structure of Bovine Matrix Gla Protein, A New Vitamin K-Dependent Bone Protein," J. Biol. Chem. (1985), 260:14971–14975.

Price et al., "Molecular Cloning of Matrix Gla protein: Implications for Substrate Recognition by the Vitamin K-Dependent γ-Dependent γ-carboxylase," Proc. Natl. Acad. Sci. USA (1987), 84:8335–8339.

Kiefer et al., "The cDNA and Derived Amino Acid Sequences for Human and Bovine Matrix Gla Protein," Nucl. Acids Res. (1988), 16:5213–5214.

Urist, "Bone: Formation by Autoinduction," Science (1965), 150:893–899.

Urist, "A bone matrix calcification-initiator noncollagenous protein," Am. J. Physiol. (1977), 232:C115–C127.

Bauer et al., "Human Osteosarcoma-Dervied Soluble Bone Morphogenetic Protein," Clin. Ortho. (1981), 154:291–295.

Conover et al., "Dentin Matrix Bone Morphogenetic Protein," ed. by Arthur Vels in Chem. Biol. Min. Corr. Tissue, (1981), pp. 597–606.

Urist et al., "A bovine low Molecular Weight Bone Morphogenetic Protein (BMP) Fraction," Clin. Ortho. (1981), 162:219–232.

Urist et al., "Bone Cell Differentiation and Growth Factors," Science, (1983), 220:680–686.

Urist et al., "Human Bone Morphogenetic Protein," Proc. Soc. Exp. Biol. Med. (1983), 173:194–199.

Sato et al., "Bone Morphogenetic Protein-induced Cartilage Development in Tissue Culture," Clin. Ortho. (1984), 183:180–187.

Urist et al., "Purification of bovine bone morphogenetic Protein by Hydroxyapatite Chromatography," Proc. Natl. Acad. Sci. USA (1984), 81:371–375.

Urist et al., "Preparation and Bioassy of Bone Morphogenetic Protein and Polypeptide Fragments," Barnes and Sirbaska, eds. in Meth. Enzymol. (1987), 146:294–312.

Kawamura et al., "Growth Factors, Mitogens, Cytokines, and Bone Morphogenetic Protein in Induced Chondrogenesis in Tissue Culture," Develop. Biol. (1988), 130:435–442.

Kawai et al., "Quantitative Computation of Induced Heterotopic Bone Formation by an Image Analysis System," Clin. Ortho. (1988), 233:262–267.

Termine et al., "Mineral and Collagen-binding Proteins of Fetal Calf Bone," J. Biol. Chem. (1981), 256:10403–10408.

Luyten et al., "Purification and Partial Amino Acid Sequence of Osteogenin, a Protein Initiating Bone Differentiation" J. Biol. Chem. (1989) 264:13377–13380.

Wozney et al., "Novel Regulators of Bone Formation: Molecular Clones and Activities," Science (1988), 242:1528–1534.

Neame et al., *J. Biol. Chem.* 264(10)L5474–5479 (1989).

Sambrook et al, p. 16.3 in *Molecular Cloning* (1989).

Lathe "Synthetic Oligonucleotides Probes . . . " *J. Mol. Biol.* 183:1–12 (1985).

(List continued on next page.)

*Primary Examiner*—Stephen G. Walsh

*Attorney, Agent, or Firm*—Paul B. Simboli; Amy L. Collins; Robert P. Blackburn

[57] ABSTRACT

The isolation, identification and production by recombinant methods of bone calcification factor, a 22 KD polypeptide, are disclosed. The peptide has calcification-inducing activity when implanted with matrix Gla protein into mammals.

24 Claims, 12 Drawing Sheets

OTHER PUBLICATIONS

Huynh et al "Constructing and Screening cDNA Libraries . . . " pp. 49–78 in *DNA Cloning* (1985).

Superti–Furga et al, "Complementary DNA Sequence and Chromosomal Mapping . . . " *Genomics* 17:463–467 (1993).

Cousen, L.S. et al., *Gene,* 61:265–275, 1987.

Cunningham, B.A. et al., *Biochemistry,* 12(24):4811–4822, 1983.

Maniatis, T. et al., *Molecular Cloning: A Laboratory Manual,* Cold Spring Harbor, New York, 1982.

FIG. 1A

```
HUMAN   GCCAAAATCCCAGGCAGC ATG GAC CTC AGT CTT CTC TGG GTA CTT CTG CCC
BOVINE      AGAAGCCCAGACGGC ATG GAC CTC ACT CTT CTG TGG GTG CTT CTG CCA
        |←Ost 1-7          -17                            -10      |←Ost
HUMAN                      MET ASP LEU SER LEU LEU TRP VAL LEU LEU PRO
BOVINE                     MET ASP LEU THR LEU LEU TRP VAL LEU LEU PRO

HUMAN   CTA GTC ACC ATG GCC TGG GGC CAG TAT GGC GAT TAT GGA TAC CCA TAC
BOVINE  CTG GTC ACC GTG GCT TGG GGA CAG TAT GGT GAC TAT GGG TAC TCC TAT
                                -1 ↓ 1            |←Ost 3-7
HUMAN   LEU VAL THR [MET] ALA TRP GLY GLN TYR GLY ASP TYR GLY TYR [PRO] TYR
BOVINE  LEU VAL THR [VAL] ALA TRP GLY GLN TYR GLY ASP TYR GLY TYR [SER] TYR

HUMAN   CAG CAG TAT CAT GAC TAC AGC GAT GAT GGG TGG GTG AAT TTG AAC CGG
BOVINE  CAT CAG TAC CAT GAC TAC AGT GAC GAT GGG TGG GTG AAT CTG AAC CGG

HUMAN   [GLN] GLN TYR HIS ASP TYR SER ASP ASP GLY TRP VAL ASN LEU ASN ARG
BOVINE  [HIS] GLN TYR HIS ASP TYR SER ASP ASP GLY TRP VAL ASN LEU ASN ARG

HUMAN   CAA GGC TTC AGC TAC CAG TGT CCC CAG GGG CAG GTG ATA GTG GCC GTG
BOVINE  CAG GGC TTC AGC TAC CAG TGT CCC CAC GGG CAG GTG GTG GTG GCC GTG

HUMAN   GLN GLY LEU SER TYR GLN CYS PRO [GLN] GLY GLN VAL [ILE] VAL ALA VAL
BOVINE  GLN GLY LEU SER TYR GLN CYS PRO [HIS] GLY GLN VAL [VAL] VAL ALA VAL

HUMAN   AGG AGC ATC TTC AGC AAG AAG GAA GGT TCT GAC AGA CAA TGG AAC TAC
BOVINE  AGG AGC ATC TTC AAC AAG AAG GAA GGT TCC GAC AGA CAG TGG AAC TAC

HUMAN   ARG SER ILE PHE [SER] LYS LYS GLU GLY SER ASP ARG GLN TRP ASN TYR
BOVINE  ARG SER ILE PHE [ASN] LYS LYS GLU GLY SER ASP ARG GLN TRP ASN TYR

HUMAN   GCC TGC ATG CCC ACG CCA CAG AGC CTC GGG GAA CCC ACG GAG TGC TGG
BOVINE  GCC TGC ATG CCC ACA CCC CAG AGC CTG GGG GAG CCT ACG GAG TGC TGG

HUMAN   ALA CYS MET PRO THR PRO GLN SER LEU GLY GLU PRO THR GLU CYS TRP
BOVINE  ALA CYS MET PRO THR PRO GLN SER LEU GLY GLU PRO THR GLU CYS TRP

HUMAN   TGG GAG GAG ATC AAC AGG GCT GGC ATG GAA TGG TAC CAG ACG TGC TCC
BOVINE  TGG GAG GAG ATC AAC AGG GCT GGA ATG GAA TGG TAC CAG ACA TGC TCC

HUMAN   TRP GLU GLU ILE ASN ARG ALA GLY MET GLU TRP TYR GLN THR CYS SER
BOVINE  TRP GLU GLU ILE ASN ARG ALA GLY MET GLU TRP TYR GLN THR CYS SER
```

FIG. 1B

```
HUMAN  AAC AAT GGG CTG GTG GCA GGA TTC CAG AGC CGC TAC TTC GAG TCA GTG
BOVINE AAC AAT GGA CTG GTG GCA GGA TTC CAG AGC CGC TAC TTC GAG TCA GTG

HUMAN  ASN ASN GLY LEU VAL ALA GLY PHE GLN SER ARG TYR PHE GLU SER VAL
BOVINE ASN ASN GLY LEU VAL ALA GLY PHE GLN SER ARG TYR PHE GLU SER VAL

HUMAN  CTG GAT CGG GAG TGG CAG TTT TAC TGT TGT CGC TAC AGC AAG AGA TGC
BOVINE CTG GAT CGC GAG TGG CAA TTT TAC TGC TGT CGC TAC AGC AAG AGA TGC

HUMAN  LEU ASP ARG GLU TRP GLN PHE TYR CYS CYS ARG TYR SER LYS ARG CYS
BOVINE LEU ASP ARG GLU TRP GLN PHE TYR CYS CYS ARG TYR SER LYS ARG CYS

HUMAN  CCA TAT TCC TGC TGG CTA ACA ACA GAA TAT CCA GGT CAC TAT GGT GAG
BOVINE CCA TAT TCC TGC TGG CTG ACA ACA GAA TAT CCA GGC CAC TAT GGT GAG

HUMAN  PRO TYR SER CYS TRP LEU THR THR GLU TYR PRO GLY HIS TYR GLY GLU
BOVINE PRO TYR SER CYS TRP LEU THR THR GLU TYR PRO GLY HIS TYR GLY GLU

HUMAN  GAG ATG GAC ATG ATT TCC TAC AAT TAT GAT TAC TAT ATC CGA GGA GCA
BOVINE GAG ATG GAC ATG ATT TCC TAC AAT TAT GAT TAC TAT ATG CGA GGG GCA

HUMAN  GLU MET ASP MET ILE SER TYR ASN TYR ASP TYR TYR [ILE] ARG GLY ALA
BOVINE GLU MET ASP MET ILE SER TYR ASN TYR ASP TYR TYR [MET] ARG GLY ALA

HUMAN  ACA ACC ACT TTC TCT GCA GTG GAA AGG GAT CGC CAG TGG AAG TTC ATA
BOVINE ACA ACC ACT TTC TCT GCA GTG GAA AGG GAT CGC CAG TGG AAA TTC ATA

HUMAN  THR THR THR PHE SER ALA VAL GLU ARG ASP ARG GLN TRP LYS PHE ILE
BOVINE THR THR THR PHE SER ALA VAL GLU ARG ASP ARG GLN TRP LYS PHE ILE

HUMAN  ATG TGC CGG ATG ACT GAA TAC GAC TGT GAA TTT GCA AAT GTT TAG
BOVINE ATG TGC CGG ATG ACT GAC TAT GAC TGT GAA TTT GCA AAT GTT TAG

HUMAN  MET CYS ARG MET THR [GLU] TYR ASP CYS GLU PHE ALA ASN VAL *
BOVINE MET CYS ARG MET THR [ASP] TYR ASP CYS GLU PHE ALA ASN VAL *
```

FIG. 1C

Human

GLN TYR GLY ASP TYR GLY TYR

PRO TYR GLN GLN TYR HIS ASP TYR SER ASP ASP GLY TRP VAL ASN LEU

ASN ARG GLN GLY LEU SER TYR GLN CYS PRO GLN GLY GLN VAL ILE VAL

ALA VAL ARG SER ILE PHE SER LYS LYS GLU GLY SER ASP ARG GLN TRP

ASN TYR ALA CYS MET PRO THR PRO GLN SER LEU GLY GLU PRO THR GLU

CYS TRP TRP GLU GLU ILE ASN ARG ALA GLY MET GLU TRP TYR GLN THR

CYS SER ASN ASN GLY LEU VAL ALA GLY PHE GLN SER ARG TYR PHE GLU

SER VAL LEU ASP ARG GLU TRP GLN PHE TYR CYS CYS ARG TYR SER LYS

ARG CYS PRO TYR SER CYS TRP LEU THR THR GLU TYR PRO GLY HIS TYR

GLY GLU GLU MET ASP MET ILE SER TYR ASN TYR ASP TYR TYR ILE ARG

GLY ALA THR THR THR PHE SER ALA VAL GLU ARG ASP ARG GLN TRP LYS

PHE ILE MET CYS ARG MET THR GLU TYR ASP CYS GLU PHE ALA ASN VAL

Bovine

```
                                             GLN TYR GLY ASP TYR GLY TYR
SER TYR HIS GLN TYR HIS ASP TYR SER ASP ASP GLY TRP VAL ASN LEU
ASN ARG GLN GLY LEU SER TYR GLN CYS PRO HIS GLY GLN VAL VAL VAL
ALA VAL ARG SER ILE PHE ASN LYS LYS GLU GLY SER ASP ARG GLN TRP
ASN TYR ALA CYS MET PRO THR PRO GLN SER LEU GLY GLU PRO THR GLU
CYS TRP TRP GLU GLU ILE ASN ARG ALA GLY MET GLU TRP TYR GLN THR
CYS SER ASN ASN GLY LEU VAL ALA GLY PHE GLN SER ARG TYR PHE GLU
SER VAL LEU ASP ARG GLU TRP GLN PHE TYR CYS CYS ARG TYR SER LYS
ARG CYS PRO TYR SER CYS TRP LEU THR THR GLU TYR PRO GLY HIS TYR
GLY GLU GLU MET ASP MET ILE SER TYR ASN TYR ASP TYR TYR MET ARG
GLY ALA THR THR THR PHE SER ALA VAL GLU ARG ASP ARG GLN TRP LYS
PHE ILE MET CYS ARG MET THR ASP TYR ASP CYS GLU PHE ALA ASN VAL
*
```

FIG. 1E

Human

```
                                    CAG TAT GGC GAT TAT GGA TAC
CCA TAC CAG CAG TAT CAT GAC TAC AGC GAT GAT GGG TGG GTG AAT TTG
AAC CGG CAA GGC TTC AGC TAC CAG TGT CCC CAG GGG CAG GTG ATA GTG
GCC GTG AGG AGC ATC TTC AGC AAG AAG GAA GGT TCT GAC AGA CAA TGG
AAC TAC GCC TGC ATG CCC ACG CCA CAG AGC CTC GGG GAA CCC ACG GAG
TGC TGG TGG GAG GAG ATC AAC AGG GCT GGC ATG GAA TGG TAC CAG ACG
TGC TCC AAC AAT GGG CTG GTG GCA GGA TTC CAG AGC CGC TAC TTC GAG
TCA GTG CTG GAT CGG GAG TGG CAG TTT TAC TGT TGT CGC TAC AGC AAG
AGA TGC CCA TAT TCC TGC TGG CTA ACA ACA GAA TAT CCA GGT CAC TAT
GGT GAG GAG ATG GAC ATG ATT TCC TAC AAT TAT GAT TAC TAT ATC CGA
GGA GCA ACA ACC ACT TTC TCT GCA GTG GAA AGG GAT CGC CAG TGG AAG
TTC ATA ATG TGC CGG ATG ACT GAA TAC GAC TGT GAA TTT GCA AAT GTT
TAG
```

FIG. 1F

Bovine

```
                                        CAG TAT GGT GAC TAT GGG TAC
TCC TAT CAT CAG TAC CAT GAC TAC AGT GAC GAT GGG TGG GTG AAT CTG
AAC CGG CAG GGC TTC AGC TAC CAG TGT CCC CAC GGG CAG GTG GTG GTG
GCC GTG AGG AGC ATC TTC AAC AAG AAG GAA GGT TCC GAC AGA CAG TGG
AAC TAC GCC TGC ATG CCC ACA CCC CAG AGC CTG GGG GAG CCT ACG GAG
TGC TGG TGG GAG GAG ATC AAC AGG GCT GGA ATG GAA TGG TAC CAG ACA
TGC TCC AAC AAT GGA CTG GTG GCA GGA TTC CAG AGC CGC TAC TTC GAG
TCA GTG CTG GAT CGC GAG TGG CAA TTT TAC TGC TGT CGC TAC AGC AAG
AGA TGC CCA TAT TCC TGC TGG CTG ACA ACA GAA TAT CCA GGC CAC TAT
GGT GAG GAG ATG GAC ATG ATT TCC TAC AAT TAT GAT TAC TAT ATG CGA
GGG GCA ACA ACC ACT TTC TCT GCA GTG GAA AGG GAT CGC CAG TGG AAA
TTC ATA ATG TGC CGG ATG ACT GAC TAT GAC TGT GAA TTT GCA AAT GTT
TAG
```

FIG. 2

TRYPTIC FRAGMENT

```
   CYS TRP LEU THR THR GLU TYR PRO GLY HIS TYR GLY GLU GLU MET
5' TGC TGG CTG ACC ACA GAG TAC CCT GGC CAC TAT GGC GAG GAG ATG  3'
           T
Probe A

3' ACG ACC GAC TGG TGT CTC ATG GGA CCG GTG ATA CCG CTC CTC TAC  5'
           A

                                        HIS TYR GLY GLU GLU MET
                                     5' CAC TAC GGX GAA GAA ATG  3'
                                          T   T       G   G
Probe B
                                     3' GTG ATG CCX CTT CTT TAC  5'
                                          A   A       C   C
```

PROBE C
bb 1.1-7
OST 3-7
OST 3-17
OST 1-7
(A)n
Spa I (A)n
Pst I
Asp718
Nco I*
0
500
1000
1500
bp

BONE CALCIFICATION FACTOR AND RECOMBINANT PRODUCTION OF THE FACTOR NUCLEIC ACID ENCODING

This application is a continuation of application Ser. No. 07/890,362, filed May 22, 1992 (now abandoned), which is a continuation of 07/360,826, filed Jun. 2, 1989 (now abandoned).

This invention relates to a class of mature native mammalian proteins which initiates calcification and which is named herein as bone calcification factor (BCF). Representative of this class are human and bovine BCF, for which the full length coding sequences are provided herein. The BCF is provided by isolation from bone sources and by synthesis using recombinant DNA techniques.

BACKGROUND OF THE INVENTION

It is known that demineralized bone matrix induces new bone formation when implanted in the soft tissue by a process generally designated as matrix induced bone formation (see Urist, M. R., *Science,* 150: 893–899 (1965)). There have been numerous efforts to extract and identify the active material (or materials) which induces this process, and it has been generally referred to in the literature as bone morphogenetic protein(s) (BMP). It is uncertain whether BMP is a single material or a mixture of materials, and there does not appear to be agreement among the investigators as to which material, if any, is the bone morphogenetic protein.

The therapeutic use of BMP offers considerable advantages over use of traditional bone graft materials. While not intended to be limited by any theory, one hypothesis assumes that BMP transforms tissue cells into osteoblasts (cells that manufacture bone). During a process that replicates normal human fetal development, BMP-induced osteoblasts form cartilage which, over a period of several months, evolve into solid bone. Thus BMP may be useful for replacing bone that has been destroyed by disease or accident, for use in treatment of scoliosis victims, for treatment of mal- or mis-formed bone, for use in healing of a fracture, etc.

It is thus an object of the present invention to produce a functional bone calcification factor or a component thereof, which is a 22 KD protein identified by its entire amino acid sequence, which initiates calcification.

It is another object of the present invention to produce this biologically active 22 KD protein by recombinant DNA technology.

It is yet another object of the present invention to construct nucleic acid screening probes for isolation of the gene comprising the 22 KD BCF.

It is yet another object of the present invention to provide an amino acid sequence of mature 22 KD BCF which can be thus prepared by direct biochemical synthesis or from constituent amino acids by peptide synthesis, for example as by the Merrifield method, and particularly by use of automated peptide synthesis technology.

These and other objects of the invention will be apparent from the following description of the preferred embodiments and from practice of the invention.

SUMMARY OF THE INVENTION

The present invention provides a class of mature native mammalian proteins (the class is termed herein as BCF), represented by native human and bovine BCF described herein, which initiate calcification in vivo which is important for formation of bone. The human and/or bovine BCF can be used to identify and isolate other mammalian BCF proteins which may or may not be homologous (in their nucleotide and amino acid sequences) to human or bovine BCF and which exhibit the BCF biological activity. It is recognized that there may be allelic variations in BCF within a species, and such allelic variants are also within the scope of the class of proteins provided by the present invention.

The present invention further provides polypeptides which are analogs of BCF, such as BCF muteins, fusion proteins, comprising BCF or BCF domains, and BCF fragments. The term fusion protein includes a protein comprising a complete BCF sequence or a BCF domain, and a heterologous N- or C-terminal sequence (such as a signal sequence or sequence which protects the protein from degradation). A BCF mutein is a protein substantially homologous to a native BCF sequence (e.g., a minimum of about 75%, 85%, 90% or 95% homologous) wherein at least one amino acid is different. A BCF fragment or domain is an amino acid sequence of sufficient length from a BCF protein such that it is identifiable as having been derived from such BCF protein. The origin of a particular peptide can be determined, for example, by comparing its sequence to those in public databases. The present invention further provides a 22 KD bone calcification factor having the human and bovine amino acid sequences shown in FIG. 1A and 1B. The present invention also provides methods of preparing the 22 KD bone calcification factor (BCF) by recombinant DNA techniques.

The present invention provides the DNA sequence encoding BCF, which may be used to construct vectors for expression in host systems by recombinant DNA techniques.

The present invention also provides therapeutic compositions comprising BCF and matrix Gla protein (MGP) for initiating calcification and methods for inducing calcification in vertebrates by introducing in vivo at the desired site an effective calcification initiating amount of BCF and MGP. The identity of MGP was first reported by Price, Urist and Otawara in *Biochem. Biophys. Res. Comm.* 117:765–771 (1983).

BRIEF DESCRIPTION OF THE DRAWINGS

FIG. 1A and 1B depicts the DNA sequences and encoded amino acid sequences of human and bovine BCF including their signal sequences;

FIG. 1C depicts the amino acid sequence of human BCF (hBCF) without its signal peptide;

FIG. 1D depicts the amino acid sequence of bovine BCF (bBCF) without its signal peptide;

FIG. 1E depicts the DNA sequence encoding hBCF without its signal sequence;

FIG. 1F depicts the DNA sequence encoding bBCF without its signal sequence;

FIG. 2 illustrates the sequence of human BCF tryptic fragment no. 41, a two-fold degenerate 45-mer oligonucleotide probe (probe A), and a second probe B, designed therefrom, consisting of 64 18-mers which are complementary to all possible codons shown.

DETAILED DESCRIPTION OF THE INVENTION

Figure 3:
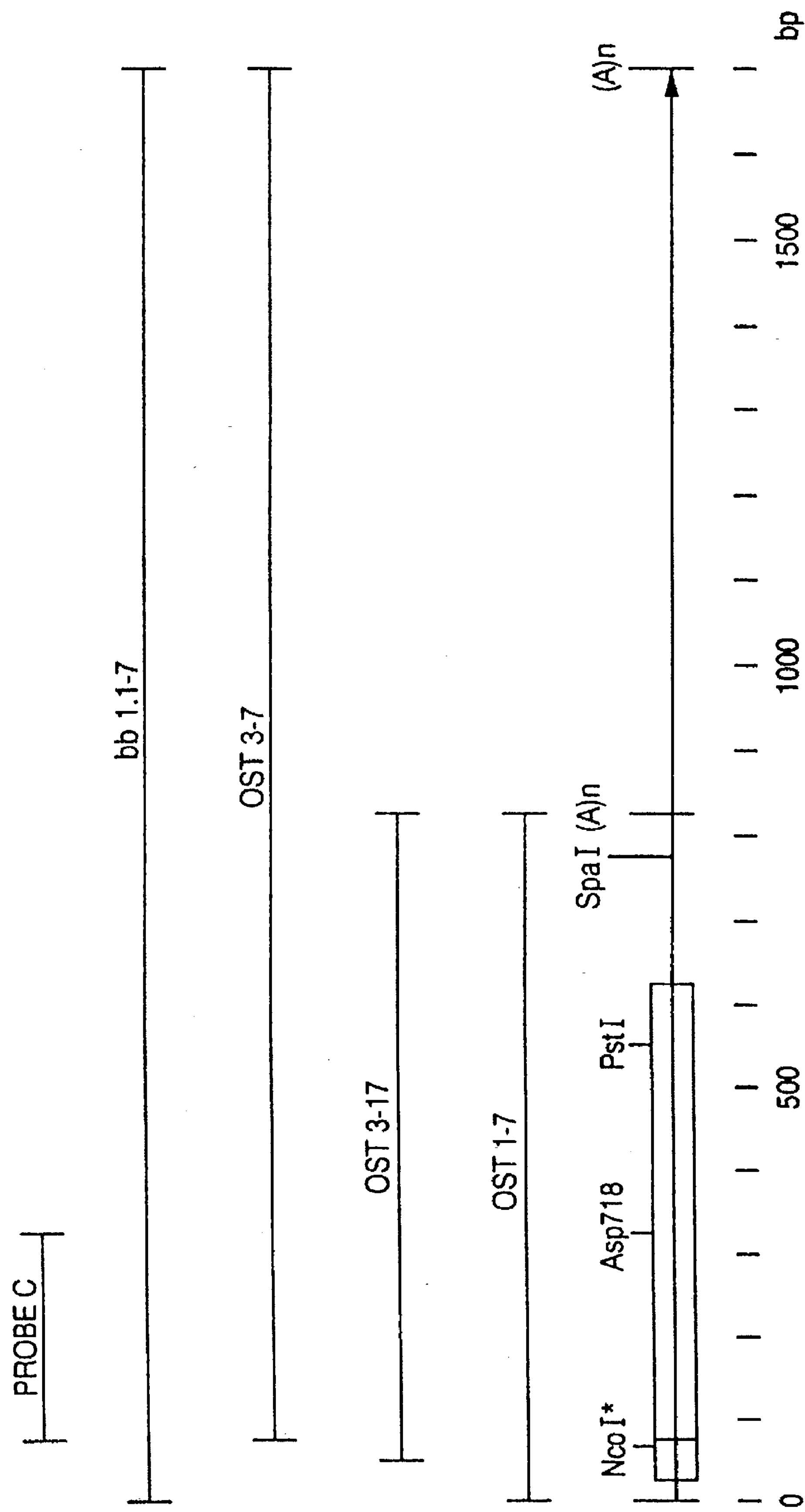
FIG. 3 illustrates probe C (derived from clone Ost 3–7) and four BCF cDNA clones isolated from a bovine cDNA library (bb1.1–7) and two human osteosarcoma cDNA libraries (Ost 1–7, Ost 3–7 and Ost 3–17). The length, coding region (boxed) and partial restriction map of the clones is included. The NcoI and SpeI sites (*) are only present in the human BCF sequences.

The BCF according to the present invention may be obtained, free of other osteoinductive associated factors, directly from bone sources, by preparative peptide synthesis using chemical methods (such as the Merrifield synthesis method) or by recombinant DNA technology.

As more particularly described in Example 1, BCF may be obtained by purification from human, bovine, or other vertebrate bone from partially purified extracts (e.g., U.S. Pat. No. 4,795,804 and references cited therein) by preparative gel electrophoresis and electroelution of the 22 K protein.

BCF may also be obtained by recombinant DNA methods, such as by screening reverse transcripts of mRNA, or by screening genomic libraries from any cell. The DNA may also be obtained by simply synthesizing the DNA using commonly available techniques and DNA synthesizing apparatus. Synthesis may be advantageous because unique restriction sites may be introduced at the time of preparing the DNA, thereby facilitating the use of the gene in vectors containing restriction sites not otherwise present in the native source. Furthermore, any desired site modification in the DNA may be introduced by synthesis, without the need to further modify the DNA by mutagenesis.

In general, DNA encoding BCF may be obtained from human, bovine or other sources by constructing a cDNA library from mRNA isolated from bones of the vertebrate; and screening with labeled DNA probes encoding portions of the human or bovine chains in order to detect clones in the cDNA library that contain homologous sequences; or by polymerase chain reaction (PCR) amplification of the cDNA (from mRNA) and subcloning and screening with labeled DNA probes; and then analyzing the clones by restriction enzyme analysis and nucleic acid sequencing so as to identify full-length clones and, if full-length clones are not present in the library, recovering appropriate fragments from the various clones and ligating them at restriction sites common to the clones to assemble a clone encoding a full-length molecule. Particularly preferred DNA probes are set forth in the accompanying examples. Any sequences missing from the library may be obtained by the 3' extension on the complementary mRNA of synthetic oligodeoxynucleotides identified by screening cDNA in the library (so-called primer extension), or homologous sequences may be supplied from known cDNAs derived from human or bovine sequences as shown in FIG. 1A and FIG. 1B.

The practice of the present invention will employ, unless otherwise indicated, conventional molecular biology, microbiology, and recombinant DNA techniques within the skill of the art. Such techniques are explained fully in the literature. See e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984).

In describing the present invention, the following terminology will be used in accordance with the definitions set out below. The term "osteoinductive associated factors" includes factors known in the art which are present in mammalian bone or other mammalian tissue and tend to co-purify with BMP or BMP activity. Such factors include proteins which have been isolated from bone having reported molecular weights of 34 KD, 24 KD, 18.5 KD, 17.5 KD, 17 KD, 16.5 KD, 14 KD (as cited in U.S. Pat. No. 4,761,471), and 6 KD (reported by Price, P. A., et al., from PNAS, 73, pp. 1447–1451, 1976).

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A DNA "coding sequence" is that portion of a DNA sequence, the transcript of which is translated into a polypeptide in vivo when placed under the control of appropriate regulatory sequences. The complementary DNA strand will be understood to be that strand which is transcribed. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the translation start codon of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences. A coding sequence is "under the control" of the promoter sequence in a cell when RNA polymerase which binds the promoter sequence transcribes the coding sequence into mRNA which is then in turn translated into the protein encoded by the coding sequence.

A cell has been "transformed" by exogenous DNA when such exogenous DNA has been introduced into the cell membrane. Exogenous DNA may or may not be integrated (covalently linked) to chromosomal DNA making up the genome of the cell. In procaryotes and yeast, for example, the exogenous DNA may be maintained on an episomal element such as a plasmid. With respect to eucaryotic cells, a stably transformed cell is one in which the exogenous DNA has become integrated into a chromosome so that it is inherited by daughter cells through chromosome replication. This stability is demonstrated by the ability of the eucaryotic cell to establish cell lines or clones comprised of a population of daughter cells containing the exogenous DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

As more particularly described in the following examples, human and bovine cDNA libraries were initially probed for sequences encoding BCF sequences using labeled oligodeoxynucleotides whose sequences were based on a partial amino acid sequence determined from analysis of purified protein samples derived from bone described herein. However, it is realized that once being provided with non-chromosomal DNA encoding human and bovine BCF and their leader sequences as described herein, one of ordinary skill in the art would recognize that other precisely hybridizing probes may be prepared from the described sequences in order to readily obtain the remainder of the desired human or bovine gene.

The non-chromosomal DNA provided by the present invention is novel, since it is believed that the naturally-occurring human and bovine genes (chromosomal) contain introns (transcribed sequences, the corresponding amino acids of which do not appear in the mature protein). Hence, the term "non-chromosomal" excludes the DNA sequences which naturally occur in the chromosomes of human or bovine cells. The present invention also encompasses the non-chromosomal cDNA sequences derivable from the DNA sequences disclosed herein.

Vectors are used to amplify the DNA which encodes the chains, either in order to prepare quantities of DNA for further processing (cloning vectors) or for expression of the chains (expression vectors). Vectors comprise plasmids, viruses (including phage), and integratable DNA fragments, i.e., fragments that are integratable into the host genome by recombination. Cloning vectors need not contain expression control sequences. However, control sequences in an expression vector include a transcriptional promoter, an optional operator sequence to control transcription, a sequence encoding suitable rRNA ribosomal binding sites (for prokaryotic expression), and sequences which control termination of transcription and translation. The expression vector should preferably include a selection gene to facilitate the stable expression of BCF and/or to identify transformants. However, the selection gene for maintaining expression can be supplied by a separate vector in cotransformation systems using eukaryotic host cells.

Suitable vectors generally will contain replicon (origins of replication, for use in non-integrative vectors) and control sequences which are derived from species compatible with the intended expression host. By the term "replicable" vector as used herein, it is intended to encompass vectors containing such replicons as well as vectors which are replicated by integration into the host genome. Transformed host cells are cells which have been transformed or transfected with vectors containing BCF encoding DNA. The expressed BCF will be deposited intracellularly or secreted into either the periplasmic space or the culture supernatant, depending upon the host cell selected and the presence of suitable processing signals in the expressed peptide, e.g. homologous or heterologous signal sequences.

Suitable host cells are prokaryotes or eukaryotic cells. Prokaryotes include Gram negative or Gram positive organisms, for example *E. coli* or bacilli. Eukaryotic cells include yeast, higher eukaryotic cells such as established cell lines of mammalian origin, or insect cells. Expression in insect cells may be accomplished using host cells and insect expression vectors as disclosed by Luckow, V. A., and Summers, M. B., *Biotechnology* 6:47–55 (1976).

Expression vectors for host cells ordinarily include an origin of replication, a promoter located upstream from the BCF coding sequence, together with a ribosome binding site, a polyadenylation site, and a transcriptional termination sequence. Those of ordinary skill will appreciate that certain of these sequences are not required for expression in certain hosts. An expression vector for use with microbes need only contain an origin of replication recognized by the host, a promoter which will function in the host and a selection gene.

An expression vector is constructed according to the present invention so that the BCF coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site. For expression of BCF in procaryotes and yeast, the control sequences will necessarily be heterologous to the coding sequence. If the host cell is a procaryote, it is also necessary that the coding sequence be free of introns (e.g., cDNA). If the selected host cell is a mammalian cell, the control sequences can be heterologous or homologous to the BMP coding sequence, and the coding sequence can either be genomic DNA containing introns or cDNA. Either genomic or cDNA coding sequences can be expressed in yeast.

Expression vectors must contain a promoter which is recognized by the host organism. Promoters commonly known and available which are used in recombinant DNA construction include the β-lactamase (penicillinase) and lactose promoter systems, a tryptophan (trp) promoter system and the tac promoter. While these are commonly used, other known microbial promoters are suitable.

In addition to prokaryotes, eukaryotic cells such as yeast are transformed with BCF encoding vectors. *Saccharomyces cerevisiae,* or common baker's yeast, is the most commonly used among lower eukaryotic host microorganisms. However, a number of other strains are commonly available and useful herein. Yeast vectors generally will contain an origin of replication from the 2 micron yeast plasmid or an autonomously replicating sequence (ARS), a promoter, DNA encoding BCF, sequences for polyadenylation and transcription termination, and a selection gene.

Suitable promoting sequences in yeast vectors include the promoters for the glycolytic enzymes such as enolase, 3-phosphoglycerate kinase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which have the additional advantage of transcription controlled by growth conditions are the promoter regions for alcohol dehydrogenase 1 or 2, isocytochrome C, acid phosphatase, as well as enzymes responsible for maltose and galactose utilization.

Higher eukaryotic cell cultures may be used, whether from vertebrate or invertebrate cells, including insects, and the procedures of propagation thereof are known. See, for example, *Tissue Culture,* Academic Press, Kruse and Patterson, editors (1973).

Suitable host cells for expressing BCF in higher eukaryotes include: monkey kidney CVI line transformed by SV40 (COS-7, ATCC CRL 1651); baby hamster kidney cells (BHK, ATCC CRL 10); chinese hamster ovary-cells-DHFR (described by Urlaub and Chasin, PNAS (USA) 77:4216 (1980)); mouse sertoli cells (TM4, Mather, J. P., *Biol. Reprod.* 23:243–251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060652, ATCC CCL 51); rat hepatoma cells (HTC, M1, 54, Baumann, M., et al., *J. Cell Biol.* 85:1–8 (1980)) and TRI cells (Mather, J. P., et al., *Annals N.Y. Acad. Sci.* 383: 44–68 (1982)). Commonly used promoters are derived from polyoma, Adenovirus 2, and Simian Virus 40 (SV40). It will be appreciated that when expressed in mammalian tissue, the recombinant BCF may have higher molecular weight due to glycosylation. It is therefore intended that partially or completely glycosylated forms of BCF having molecular weights greater than that provided by the amino acid backbone are within the scope of this invention.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Pub. Nos. GB 2,121,054; GB 2,008,123; GB 2,007,675; and European Pub. No. 103,395. Preferred procaryotic expression systems are in *E. coli.* Other preferred expression vectors are those for use in eucaryotic systems. An exemplary eucaryotic expression system is that employing vaccinia virus, which is well-known in the art. See. e.g., Macket et al. (1984) *J. Virol.* 49:857; "DNA Cloning," Vol. II, pp. 191–211, supra; PCT Pub. No. WO 86/07593. Yeast expression vectors are known in the art. See, e.g., U.S. Pat. Nos. 4,446,235; 4,443,539; 4,430,428; see also European Pub. Nos. 103,409; 100,561; 96,491. Another expression system is vector pHS1, which transforms Chinese hamster ovary cells. The use of the vector is described in PCT Pub. No. WO 87/02062, the disclosure of which is incorporated herein by reference.

Mammalian tissue can be cotransformed with DNA encoding a selectable marker such as dihydrofolate reductase (DHFR) or thymidine kinase and DNA encoding BCF. If wild type DHFR protein is employed, it is preferable to select a host cell which is deficient in DHFR, thus permitting the use of the DHFR coding sequence as marker for successful transfection in hgt$^-$ medium, which lacks hypoxanthine, glycine, and thymidine. An appropriate host cell in this case is the Chinese hamster ovary (CHO) cell line deficient in DHFR activity, prepared and propagated as described by Urlaub and Chasin, 1980, *Proc. Nat. Acad. Sci.* (USA) 77: 4216.

Recently, expression vectors derived from Baculovirus for use in insect cells have become known in the art.

Depending on the expression system and host selected, BCF is produced by growing host cells transformed by an expression vector described above under conditions whereby the BCF protein is expressed. The enzyme protein is then isolated from the host cells and purified. If the expression system secretes the enzyme into growth media, the protein can be purified directly from cell-free media. If the BCF protein is not secreted, it is isolated from cell lysates, the selection of the appropriate growth conditions and recovery methods are within the skill of the art.

The recombinantly made BCF is recovered from transformed cells in accordance with known procedures. Preferably, an expression vector will be used which provides for secretion of BCF from the transformed cells, thus the cells may be separated by centrifugation. The BCF generally is purified by general protein purification techniques, including, but not limited to, size exclusion, ion-exchange chromatography, HPLC, and the like.

Once a coding sequence for BCF has been prepared or isolated, it can be cloned into any suitable vector or replicon and thereby maintained in a composition which is substantially free of vectors that do not contain a BCF coding sequence (e.g., free of other library clones). Numerous cloning vectors are known to those of skill in the art. Examples of recombinant DNA vectors for cloning and host cells which they can transform include the various bacteriophage lambda vectors (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), actinophage, ϕC31 (Streptomyces), YIp5 (Saccharomyces), YCp19 (Saccharomyces), and bovine papilloma virus (mammalian cells). See generally, DNA Cloning: Vols. I & II, supra; T. Maniatis et al., supra; B. Perbal, supra.

It is further intended that calcification-initiating fragments of BCF are within the scope of the present invention. Such active fragments may be produced, for example, by pepsin digestion of BCF. The active fragments may be identified by the in vivo and/or in vitro assays described hereinbelow.

Alternatively the BCF may be made by conventional peptide synthesis using the principles of the Merrifield synthesis and preferably using commercial automatic apparatus designed to employ the methods of the Merrifield synthesis. Peptides prepared using the Merrifield synthesis may be purified using conventional affinity chromatography, gel filtration and/or RP-HPLC.

FIG. 1A and FIG. 1B shows the aligned nucleotide and deduced amino acid sequences for both bovine and human BCF for maximum amino acid sequence identity. Amino acids not conserved in both species are boxed. The putative initiation codon is located at position −17 followed by a stretch of amino acids showing strong hydrophobicity characteristics of signal peptides. A putative signal peptide cleavage site is indicated by the arrow. The putative mature proteins begin at position 1(Gln), and contain 183 amino acids, of which 96.2% are identical. The derived molecular weight of human BCF is 21,967 and for bovine BCF is 21,984. The underlined sequences are those from which the oligonucleotide probes are derived. Substantially pure BCF, higher molecular glycosylated forms thereof, or active fragments thereof, or the nontoxic salts thereof, combined with a pharmaceutically acceptable carrier to form a pharmaceutical composition, may be administered to mammals, including humans, either intravenously, subcutaneously, percutaneously, intramuscularly or orally.

Such proteins are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

Pharmaceutical compositions will usually contain an effective amount of BCF in conjunction with a conventional, pharmaceutically acceptable carrier. The dosage will vary depending upon the specific purpose for which the protein is being administered, and dosage levels in the range of about 0.1 μg to about 100 milligrams per Kg. of body weight may be used. Implants of recombinant BCF, when mixed with matrix Gla protein (MGP) (see Example 7), will initiate calcification. The BCF may be either the human or bovine form or mixtures thereof. Similarly, the MGP may be any mammalian form thereof, preferably human, bovine or mixtures thereof. Matrix Gla protein (MGP) may be isolated in the course of preparation of bone morphogenetic protein (BMP) from demineralized gelatinized bovine cortical bone by the methods of Urist et al. [See: Price et al., *Proc. Natl. Acad. Sci. USA* 73:1447, 1976; Urist, M. R., Huo, Y. K. Brownell, A. G., Hohl, W. M. Buyske, J., Lietze, A., Tempst, P., Humkapillar, M., and DeLange, R. J.: Purification of bovine bone morphogenetic protein by hydroxyapatite chromatography. *Proc. Natl. Acad. Sci.* 81:371–375, 1984 and Urist, M. R., Chang, J. J., Lietze, A., Huo, Y. K., Brownell, A. G., and DeLange, R. J.: Methods of preparation and bioassay of bone morphogenetic protein and polypeptide fragments. In: Barnes, D., and Sirbaska, D. A. (eds.): *Methods in Enzymology, vol.* 146. New York, Academic Press, 1987, pp. 294–312]. A preparation containing MGP is first separated from other bone matrix protein by hollow fiber ultrafiltration through a 10 K pore-size filter. Under dissociated conditions in 6M urea and 0.02 M edetic acid (EDTA), the MGP assumes an elongated structure in which proteins with 14 to 15 K molecular weight ($M_r$) pass through a 10 K filter. The MGP is further purified by ion exchange chromatography (Berg, R. A. In: Methods in Enzymology, 1982, vol. 82:372–398).

Furthermore, to initiate calcification BCF and MGP may be mixed with any combination of one or more other proteins, particularly, with one or more other proteins derived from bone. Such mixtures may not only initiate calcification, but may also induce cartilage formation and bone growth.

Implants of mixtures of BCF and MGP induce calcification in the quadriceps compartment. The BCF cDNA may also be utilized in a diagnostic test for identifying subjects having defective BCF-genes, defective BCF or autoantibodies directed against BCF; or to detect levels of BCF, which may be an indication of osteoporosis.

Preparations of BCF may be assayed in vivo according to the method described by Urist et al., *Methods in Enzymology* (D. Barnes and D. A. Sirbaska, Eds.), vol. 146, pp. 294–312, Academic Press, N.Y. (1987), and in vitro by the method of Sato and Urist, *Clin. Orthop.,* 183:180–187 (1984) as modified by Kawamura and Urist, *Dev. Biol.,* 130:435–442 (1988), all of which are incorporated by reference herein.

It is preferred that the BCF be admixed with matrix Gla protein (MGP) to form a delivery system comprising these two proteins. The amount of MGP in the composition is not believed to be critical and, for convenience, equal portions of BCF and MGP may be used in dosages in the range of about 0.1 μg (combined weight of BCF and MGP) to 100 mg/Kg. body weight.

The BCF and MGP may be implanted as a time-release composition encapsulated, for instance, in liposomes or other time-release membranes, natural or synthetic, which are absorbable by the host subject. The purification protocols, described in detail below, allow for the first time the purification of native BCF in sufficient quantity and at a high enough purity to permit accurate amino acid sequencing. The amino acid sequences derived from the purified BCF allow for the design of probes to aid in the isolation of native BCF nucleic acid sequence, or the design of synthetic nucleic acid sequences encoding the amino acid sequence of BCF.

Specific anti-sera or monoclonal antibodies (described below) can be made to a synthetic or recombinant BCF peptide having the sequence or fragments of the sequence of amino acid residues, such as those shown in FIGS. 1C or 1D. An example is the tryptic fragment shown in FIG. 2, and antibodies thereto can be used to immunoprecipitate any BCF present in a selected tissue, cell extract, or body fluid. Purified BCF from this source can then be sequenced and used as a basis for designing specific probes as described above. Antibodies to other regions that diverge from known BCF can also be used. Also useful as antigens are purified native or recombinant BCF.

As mentioned above, a DNA sequence encoding BCF can be prepared synthetically rather than cloned. The DNA sequence can be designed with the appropriate codons for the BCF amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair, et al. (1984) *Science* 223:1299; Jay et al. (1984) *J. Biol. Chem.* 259:6311.

Synthetic DNA sequences allow convenient construction of genes which will express BCF analogs or "muteins". Alternatively, DNA encoding muteins can be made by site-directed mutagenesis of native BCF genes or cDNAs, and muteins can be made directly using conventional polypeptide synthesis. Muteins altered, for example, by the substitution of acidic residues (e.g., Glu or Asp) could have reduced activity toward membrane-bound or complex substrates or have anti-sense therapeutic uses for overproduction of BCF.

Site-directed mutagenesis is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Native, recombinant or synthetic BCF peptides (full length or subunits) can be used to produce both polyclonal and monoclonal antibodies. If polyclonal antibodies are desired, purified BCF peptide is used to immunize a selected mammal (e.g., mouse, rabbit, goat, horse, etc.) and serum from the immunized animal later collected and treated according to known procedures. Compositions containing polyclonal antibodies to a variety of antigens in addition to BCF can be made substantially free of antibodies which are not anti-BCF by immunoaffinity chromatography.

Monoclonal anti-BCF antibodies can also be readily produced by one skilled in the art form the disclosure herein. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against BCF peptides can be screened for various properties; i.e., isotype, epitope, affinity, etc. Of particular interest are monoclonal antibodies that neutralize the activity of BCF. Such monoclonals can be readily identified in BCF activity assays. High affinity antibodies are also useful in immunoaffinity purification of native or recombinant BCF.

Antibodies to BCF forms described herein (both polyclonal and monoclonal) may be used to inhibit or to reverse arterial calcification. An appropriate therapeutic method would be to treat the patient with an effective dose of anti-BCF antibodies through a conventional intravenous route. In the treatment of local, acute inflammation, treatment with anti-BCF antibody would be indicated, perhaps by intramuscular injection. These compositions may also be useful in targeting various forms of tumors, since tumors are known to sometimes calcify, suggesting the presence of BCF. BCF antagonists, such as BCF muteins, could also be used in place of antibodies.

The determination of the appropriate treatment regimen (i.e., dosage, frequency of administration, systemic vs. local, etc.) is within the skill of the art. For administration, the antibodies will be formulated in a unit dosage injectable form (solution, suspension, emulsion, etc.) in association with a pharmaceutically acceptable parenteral vehicle. Such vehicles are usually nontoxic and nontherapeutic. Examples of such vehicles are water, saline, Ringer's solution, dextrose solution, and Hank's solution. Nonaqueous vehicles such as fixed oils and ethyl oleate may also be used. A preferred vehicle is 5% (w/w) human albumin in saline. The vehicle may contain minor amounts of additives, such as substances that enhance isotonicity and chemical stability, e.g., buffers and preservatives. The antibody is typically formulated in such vehicles at concentrations of about 1 μg/ml to 10 mg/ml.

Anti-BCF antibodies will also be useful in diagnostic applications. The present invention contemplates a method, particularly a diagnostic method, in which a sample from a human (or other mammal) is provided, and the amount of BCF is quantitatively measured in an assay. For example, employing anti-BCF antibodies in a quantitative immunoassay could be used to detect genetic deficiency in BCF. Antibody specific for BCF could be formulated into any conventional immunoassay format; e.g., homogeneous or heterogeneous, radioimmunoassay or ELISA. The various formats are well known to those skilled in the art. See, e.g., "Immunoassay" A Practical Guide" (D. W. Chan and M. T. Peristein, eds. 1987) the disclosure of which is incorporated herein by reference.

In general, recombinant production of BCF can provide compositions of that BCF substantially free of other proteins having osteoinductive associated functions. The ability to obtain high levels of purity is a result of recombinant expression systems which can produce BCF in substantial quantities vis-a-vis in vivo sources. Thus, by applying conventional techniques to recombinant cultures, BCF compositions can be produced that are substantially more pure than the compositions available from bone sources.

Purified BCF will be particularly useful as a tool in the design and screening of calcification inhibitors. First, milligram amounts of the material are obtainable according to the present invention. Milligram amounts are capable of crystallization to permit three dimensional studies using X-ray diffraction and computer analysis. This may permit deduction concerning the shape of the molecule, thus defining proper shapes for substances usable as inhibitors of the activity normally exhibited by BCF. Generally, antagonists have been "peptides" whose interactions with a factor which is inhibited are stabilized by modification of the "residues" participating in the peptide bond so as to enhance the ability of the "peptide" to interact specifically with converting factor. Thus the peptide bond joins specifically chosen carboxylic acids and amines (not necessarily amino acids). These "peptides" are configured in a three dimensional array so as to complement the contours of the intended target, converting enzyme. A similar lock and key spatial arrangement may result from molecules designed complementary to the surface contours of the BCF of the invention. It is understood that "surface" includes convolutions which may face inward, and specifically includes the active site. Furthermore, "complementary" is understood to mean that, in addition to spatial conformations which "fit", interactions between the protein and the molecule which matches its surface contours are attractive and positive. These interactions may be hydrogen bonding, ionic, or hydrophobic affinity.

Accordingly, the invention contemplates peptide antagonists or agonists (2–15 amino acids) to BCF which are characterized by three dimensional contours complementary to the three dimensional contours on the surface of recombinant BCF. By peptide in this context is meant that the antagonist or agonist contains carboxylic acid amide bonds corresponding to one less than the number of residues. The carboxylic acid and amine participants need not be α-amino acids.

Second, even without the assistance of a three dimensional structure determination, purified BCF of the invention is of significance as a reagent in screening BCF inhibitors in vitro as an ad hoc approach to evaluation. Impure BCF preparations currently available yield confusing data due to the impact of the impurities on the test results. For example, contaminants which turn out to be themselves inhibitors, activators, or substrates for BCF may interfere with the evaluation. Thus, a substantial improvement in current screening techniques for BCF inhibitors would be effected by the availability of the purified BCF protein.

It will be understood that this description and disclosure of the invention is intended to cover all changes and modifications of the invention which are within the spirit and scope of the invention. It is within the knowledge of the art to insert, delete or substitute amino acids within the amino acid sequence of a BCF without substantially affecting the calcification and bone growth inducing activity of the molecule. The invention is expressly stated to be broad enough to include intentional deletions, additions or substitutions. Furthermore, it is recognized that one skilled in the art could recombinantly produce such modified proteins.

Native, recombinant or synthetic BCF peptides (full length or subunits) can be further used to produce both polyclonal and monoclonal antibodies. If polyclonal antibodies are desired, purified BCF is used to immunize a selected mammal (e.g., mouse, rabbit, goat, horse, etc.) and serum from the immunized animal later collected and treated according to known procedures. Compositions containing polyclonal antibodies to a variety of antigens in addition to BCF can be made substantially free of antibodies which are not anti-BCF by immunoaffinity chromatography.

Monoclonal anti-BCF antibodies can also be readily produced by one skilled in the art from the disclosure herein. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hamerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887, 4,451,570; 4,466,917; 4,472,500; 4,491,632; 4,493,890.

Panels of monoclonal antibodies produced against BCF peptides can be screened for various properties; i.e., isotype, epitope, affinity, etc. Of particular interest are monoclonal antibodies that neutralize the activity of BCF. Such monoclonals can be readily identified in BCF activity assays. High affinity antibodies are also useful in immunoaffinity purification of native or recombinant BCF.

Anti-BCF antibodies will also be useful in diagnostic applications. For example, bone isolated from osteoporosis patients may show that it is deficient in BCF. Thus, the present invention contemplates a method, particularly a diagnostic method, in which a bone sample from a human (or other mammal) is provided, and the amount of BCF is quantitatively measured in an assay. Antibody specific for BCF could be formulated into any conventional immunoassay format; e.g., homogeneous or heterogeneous, radioimmunoassay or ELISA. The various formats are well known to those skilled in the art. See, e.g., "Immunoassay: A Practical Guide" (D. W. Chan and M. T. Peristein, eds. 1987) the disclosure of which is incorporated herein by reference. Quantitative assays other than immunoassays could also be used to measure the relative levels of BCF compared to a standard or prior observed BCF level in a patient. The following examples are provided by way of illustration but are not intended to limit the invention in any way.

EXAMPLE 1

Sequence Analysis of BCF

The 22 K proteins of interest, partially purified from human and bovine sources as described by Urist, et al., *Proc. Nat. Acad. Sci. USA,* 81, 371–375 (1984), were further purified to homogeneity by preparative gel electrophoresis and electroelution (M. W. Hunkapiller, E. Lujan, F. Ostrander and L. E. Hood, *Methods in Enzymology,* 91:227–236 (1983)). This purification showed that the initial partially purified samples contained, in addition to the 22 K BCF, other mammalian proteins at 34 K, 19 K, 14 K and 6 K. After precipitation with acetone (W. H. Konigsberg and L. Henderson, *Methods in Enzymology,* 91:254–259 (1983)) and quantitation by amino acid analysis (B. A. Bidlingmeyer, S. A. Cohen and T. L. Tarvin, *Journal of Chromatography,* 336:93–104 (1984)), the material was reduced under denaturing conditions with 2-mercaptoethanol and cysteine residues were derivatized with 4-vinyl-pyridine (M. Friedman, L. G. Krull and J. F. Cavins, *Journal of Biological Chemistry,* 245:3868–3871 (1970)). After exhaustive dialysis to remove the denaturant, protein recovery was assessed by a repetition of amino acid analysis. The proteins were digested with TPCK-trypsin in the presence of 2M urea to generate unblocked peptide fragments suitable for sequence analysis (G. Allen, *Sequencing of Proteins and Peptides*, pages 51–62 (1981), Elsevier/North Holland Publishing Company, Amsterdam, Holland). Products of the digestion were resolved by reverse-phase high performance liquid chromatography using gradients of acetonitrile or acetonitrile/isopropanol in aqueous trifluoroacetic acid (J. E. Shively, *Methods of protein Microcharacterization*, pages 41–87 (1986), Humana Press, Clifton, N.J.). Peptide fractions were subjected to automated Edman degradation using an Applied Biosystems 470A protein sequencer (M. W. Hunkapiller, R. M. Hewick, W. J. Dreyer and L. E. Hood, *Methods in Enzymology*, 91:399–413 (1983)). The phenylthiohydantoin amino acid derivatives were identified by chromatography on an Applied Biosystems 120A PTH analyzer (M. W. Hunkapiller, *Applied Biosystems*, User Bulletin Number 14 (1985), Applied Biosystems, Foster City, Calif.). The hBCF sequence determined by this method is confirmed by the sequence deduced from the human cDNA in FIG. 1A and 1B.

EXAMPLE 2

RNA Isolation mRNA was isolated from fresh 7-month old calf bones (obtained from Rancho Veal Meat Packers, Petaluma, Calif.) or from human osteosarcoma cells.

Calf femur midshafts were scraped free of connective tissue and marrow, broken into coarse fragments, and frozen at −80° C. Human osteosarcoma cells were also frozen at −80° C. RNA was isolated from both the frozen tissues by the guanidinium thiocyanate/CsCl method (Maniatis, T., Fritsch, E. F. and Sambrook, J. *Molecular Cloning: A Laboratory Manual* (Cold Spring Harbor Lab., Cold Spring Harbor, N.Y. (1982); Freeman, G. J., Clayberger, C., DeKruyff, R., Rosenblum, D. S. and Cantor, H. *Proc. Natl. Acad. Sci.: USA*, 80: 4094–4098 (1983)). A blender (OSTERIZER™) was used to pulverize the bovine tissue directly in the guanidinium thiocyanate extraction solution. Poly$(A)^+$ RNA was purified by a single fractionation over oligo(dT)-Cellulose (Maniatis, et al., supra).

Construction of the cDNA Libraries

First strand cDNA was synthesized from bovine matrix or human osteosarcoma poly$(A)^+$ RNA using conditions similar to Okayama and Berg (Okayama, H. and Berg, P. *Molec. and Cell Biol.* 3: 4094–4098 (1983)). About 5 μg of poly$(A)^+$ RNA in 20 μl 5 mM tris-hydrochloride (pH 7.5) was heated to 65° C. for 3 min, then quick cooled on wet ice and immediately adjusted (at room temperature) to contain 50 mM Tris-hydrochloride (pH 8.3 at 42° C.), 8 mM $MgCl_2$, 30 mM KCl, 10 mM dithiothreitol, 2 mM each of dATP, dGTP, dTTP and [α-$^{32}$p] dCTP(~300 cpm/pmol), 60 units RNasin, and 2.5 μg oligo $(dT)_{12-18}$ (total volume 40 ml). The reaction was initiated by the addition of 50–60 units of cloned moloney murine leukemia virus reverse transcriptase and continued for 60 min at 42° C. Double-stranded (ds) cDNA synthesis and EcoRI linker addition were performed by two different methods. Initially, the second cDNA strand was synthesized by the method of Wickens et al. (Wickens, M. P., Buell, G. N. and Schimke, R. T. *J. Biol. Chem.* 253:2483–2495 (1978)). The hairpin loop was removed from the ds cDNA by SI nuclease, methylated with EcoRI methylase, made blunt-ended with $T_4$ DNA polymerase, ligated to phosphorylated EcoRI linkers and finally digested with EcoRI (Maniatis, et al., supra). Later, the second cDNA strand was synthesized by the method of Gubler and Hoffman (Gubler, U. and Hoffman, B. J. *Gene* 25:263–269 (1983)) as modified by Aruffo and Seed (Aruffo, A. and Seed, B. *Proc. Natl. Acad. Sci.: USA* 74:8573–8577 (1987)). The ds cDNA was then ligated to asymmetrically (hemi) phosphorylated EcoRI adapters (see oligonucleotide synthesis) as described by Aruffo and Seed, supra, phosphorylated with $T_4$ polynucleotide kinase (Maniatis, et al., supra), adjusted to 0.5M NaCl, 25 mM EDTA and heated at 75° C. for 15 min to inactivate the polynucleotide kinase. The ds cDNA prepared by both procedures was separated from unligated linkers/adapters by chromatography on Biogel A-15 m and recovered by ethanol precipitation. cDNA was ligated to λZAP arms (Stratagene) with $T_4$ DNA ligase (New England Biolabs) as described by supplier, but included 15% polyethylene glycol (PEG) 8000 (Sigma), a modification described by Pfeiffer and Zimmerman (Pheiffer, B. H. and Zimmerman, S. B. *Nucl. Acids Res.* 11:7853–7871 (1983)). The ligated DNA was recovered by centrifugation (12,000 xg), washed with chloroform, dried, resuspended in 4 μl water and incubated with an in vitro packaging extract (Stratagene) according to supplier. Recombinant phage were propagated in *E. coli* BB4 (Stratagene).

EXAMPLE 3

Synthesis of Oligonucleotides

Oligonucleotides were synthesized by the phosphoramidite method with an Applied Biosystems (Foster City, Calif.) model 380A synthesizer, purified by polyacrylamine gel electrophoresis and desalted on a Waters SEP-PAK ($^C$18) cartridge. A 10-mer oligonucleotide (5'CCGAATTCGG3') was synthesized and used as the EcoRI linker for cDNA library construction. Prior to ligation, the linker was phosphorylated with $T_4$ polynucleotide kinase (Maniatis, T., Fritsch, E. F. and Sambrook, J., *Molecular Cloning: A Laboratory Manual* (Cold Spring Harbor Lab., Cold Spring Harbor, N.Y., 1982)). A 14-mer oligonucleotide (5'CCTGTAGATCTCCG3') and a 18-mer oligonucleotide (5'AATTCGGAGATCTACAGG3') were synthesized and used as the EcoRI adapters. The 14-mer was phosphorylated (Maniatis, et al., supra) and subsequently heated to 95° C. for 15 min to inactivate polynucleotide kinase, prior to annealing with the 18-mer. These asymmetrically phosphorylated adapters also contained an internal BglII restriction enzyme site. Based on the amino acid sequence of the human BCF tryptic fragment, a two-fold degenerate 45-mer oligonucleotide probe was designed (FIG. 2, probe A) following the rules of Lathe (Lathe, R., *J. Mol. Biol.* 183: 1–12 (1985)). The two oligonucleotide probes (A and B) were synthesized based on the amino acid sequence of a purified tryptic peptide of the human bone calcification factor (hBCF) (FIG. 2).

EXAMPLE 4

Screening of the cDNA Libraries a. Human osteosarcoma libraries.

Approximately 300,000 recombinant phage were plated (50,000 phage/137 mm dia. plate) in *E. coli* BB4, grown for 5–6 h at 37° C., transferred to nitrocellulose filters (Millipore, HATF 137), processed according to Benton and Davis (Benton, W. D. and Davis, R. W., *Science* 196:180 (1977)) and screened with oligonucleotide probe A. Eighteen putative hBCF cDNA clones from 300,000 recombinants were identified. Southern blot analyses (described below) of the cDNA inserts were performed using probe A and also probe B (FIG. 2), a fully degenerate 18-mer oligonucleotide contained within probe A. Most of the clones hybridized to both probes. The probe was end-labeled with $T_4$ polynucleotide kinase and [$\gamma^{32}$-P]ATP (Maniatis, et al., supra) to a specific activity of $1–2\times10^8$ cpm/μg. The filters were prehybridized for 1–2 h at 37° C. in 20% (vol/vol) formamide, 5×SSC (1×SSC=0.15 M sodium chloride/0.15 M sodium citrate, pH 7), 5× Denhardt's solution (1× Denhardt's solution=0.02% polyvinylpyrrolidone/0.02% Ficoll/0.02% bovine serum albumin), 10% dextran sulfate, 50 mM sodium phosphate pH 6.8, 1 mM sodium pyrophosphate, 0.1% $NaDodSO_4$ and 50 μg/ml denatured salmon sperm DNA. Labeled probe was added to a concentration of $10^6$ cpm/ml and hybridization was continued overnight at 37° C. with gentle shaking. The filters were washed twice (20 min/wash) in 2XSSC, 0.1% $NaDodSO_4$ at 55° C. and exposed to Kodak XAR-2 film with a Dupont Lightning Plus intensifying screen overnight at −80° C. Areas of plaques giving signals on duplicate filters were picked, replated and rescreened as above until pure plaques were obtained.

Two of the double positive clones (Ost 3–7 and Ost 3–17, FIG. 3) were sequenced and shown to contain identical overlapping sequences as well as a region encoding the tryptic fragment (FIG. 1A and 1B underlined and FIG. 2). Ost 3–17 contains the complete mature protein coding sequence, but not the complete signal peptide, as is evident from the bBCF cDNA shown in FIG. 1A and 1B.

An additional 300,000 recombinant phages from two different osteosarcoma cDNA libraries were later plated and screened as above but with the following changes: (1) The hybridization mix contained 40% formamide, 5×SSC, 5X Denhardt's solution, 10% PEG 8000, 50 mM sodium phosphate pH 6.8, 0.5% $NaDodSO_4$ and 50 μg/ml denatured; (2) the filters washed at 65° C. in 2×SSC, 0.1% $NaDodSO_4$; and (3) the probe was a 240 bp. DNA fragment obtained by digesting cDNA clone Ost 3–7 with BglII and Asp718 (probe C, FIG. 3). The probe was purified and labeled by the oligo-primer method (Feinberg, A. P. and Vogelstein, B., *Anal. Biochem.* 137:266–267 (1984)) to a specific activity of $>1\times10^9$ cpm/μg. Approximately 20 clones from each library gave strong hybridization signals and restriction enzyme analysis of these clones identified several that were longer than Ost 3–17. One of these, Ost 1–7 (FIG. 3), was sequenced and judged to be full length based on its homology to the bovine BCF cDNA clone, described below.

b. Bovine bone matrix cDNA library.

Approximately 300,000 recombinants from the bovine bone matrix cDNA library were screened with probe C (FIG. 3), a 240 b.p. BglII—Asp 718 DNA fragment from Ost 3–7, under the conditions described for probe A except that formamide was omitted from the hybridization solution. The filters were washed at 55° C. in 2×SSC, 0.1% $NaDodSO_4$. Twenty-four positive plaques were identified. Clone bb1.1–7 (FIG. 4B), which contained the largest insert, was sequenced and shown to contain sequences homologous to hBCF. The deduced amino acid sequence of the bBCF cDNA indicates that amino acid −4 is not the initiation codon due to the presence of a Val at this position. The most likely initiation codon is located at amino acid position −17 which is 28 nucleotides beyond the 5' end of the hBCF Ost 3–17 clone. The Met at position −17 is also preceded by an acceptable ribosome binding site.

EXAMPLE 5

Subcloning, Sequencing and Analysis

Recombinant plasmids were released in the Bluescript SK(−)vector from λZAP by the M13 rescue/excision protocol described by the supplier (Stratagene). The plasmids were propagated in *E. coli* BB4, and plasmid DNA was isolated by the alkaline lysis method (Maniatis, et al., supra). cDNA inserts were excised with either EcoRI or BglII restriction enzymes (Boehringer-Mannheim), purified by polyacrylamide gel electrophoresis (Maniatis, et al., supra) and passage over an Elutip-d column (Schleicher and Schuell) and subcloned into the M13 sequencing vectors (Yanisch-Perron, C., Viera, J. and Messing, J., *Gene* 33: 103–119 (1985)). DNA sequencing was performed by the dideoxy chain termination method (Sanger, F. Nicklen, S. and Coulson, A. R., *Proc. Natl. Acad. Sci. USA* 74: 5463–67 (1977)) using M13 primers as well as specific internal primers. Ambiguous regions were resolved 7-deaza-2-deoxyguanidine-triphosphate (Barr, P. J., Thayer, R. M., Laybourn, P., Najarian, R. C., Seela, F., and Tolan, D., Biotechniques 4:428–32 (1986)) and SEQUENASE® brand DNA polymerase (U.S. Biochemicals).

a. Northern Blot

Poly(A)$^+$ RNA was fractionated on a 1.4% agarose gel in the presence of formaldehyde (Lehrach, H., Diamond, D., Wozney, J. M. and Boedtker, H., *Biochemistry* 16:4743–51 (1977)) and directly transferred to nitrocellulose according to Thomas (Thomas, P., *Proc. Natl. Acad. Sci. USA* 77:5201–5 (1980)). Filters were hybridized with probe C as previously described (EXAMPLE 4, Screening of the cDNA Libraries) in the 40% formamide containing hybridization solution and were washed at 55° C. in 2×SSC, 0.1% $NaDodSO_4$ and 0.1×SSC, 0.1% $NaDodSO_4$ with autoradiography following each set of washings.

RNA transfer blot analysis demonstrates the presence of two mRNA forms of ≈0.9 and 1.8 kB in human osteosarcoma tissue. The two forms were also observed in human placenta but were absent in a human liver cell line, HEPG2. The two forms were also observed in bovine bone matrix cells with the larger form predominating. A trace of the large species could also be seen in bovine bone marrow. The two mRNAs are most likely generated by differential polyadenylation at the 2 sites (AATAAA) found in the 3' untranslated region.

b. Southern Blot

1. Genomic

10 μg of genomic DNA (Clontech) was digested with EcoRI, fractionated on 0.7% agarose gels and transferred to nitrocellulose according to Maniatis, et al., supra. Hybridization and washing conditions were identical to those described in a. above.

Genomic DNA transfer blot analysis suggests that hBCF and bBCF are single copy (or low copy) genes due to the few bands seen in the EcoRI digest.

2. cDNA Clones

DNA from cDNA clones were digested with EcoRI or BglII, fractionated on 1.0% agarose gels, transferred to nitrocellulose (Maniatis, et al., supra) and hybridized with probe A as previously described or with probe B in a tetramethylammonium chloride containing hybridization solution under conditions described by Wood (Wood, W. I., Gitschier, J., Laskey, L. and Lawn, R., *Proc. Natl. Acad. Sci. USA* 82: 1585–88 (1985)).

EXAMPLE 6

Expression of hBCF in Yeast

Figure 4A:
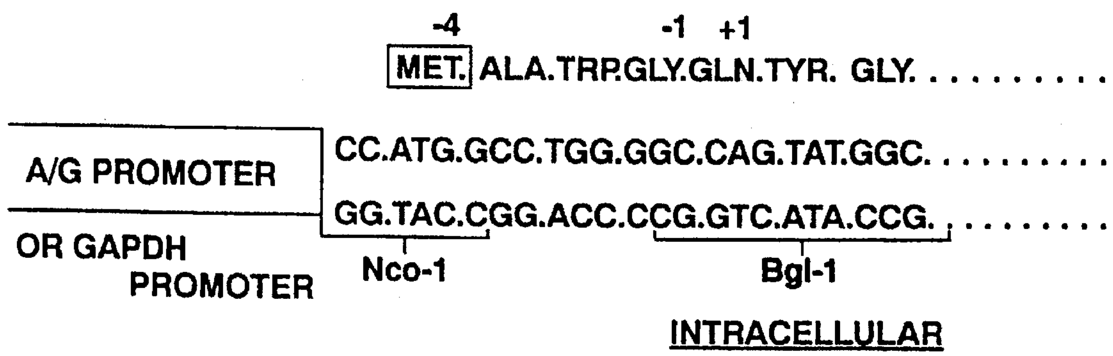
FIG. 4A illustrates the junction between the BCF-encoding DNA and promoter in an expression vector used to express unsecreted BCF in yeast.
Figure 4B:
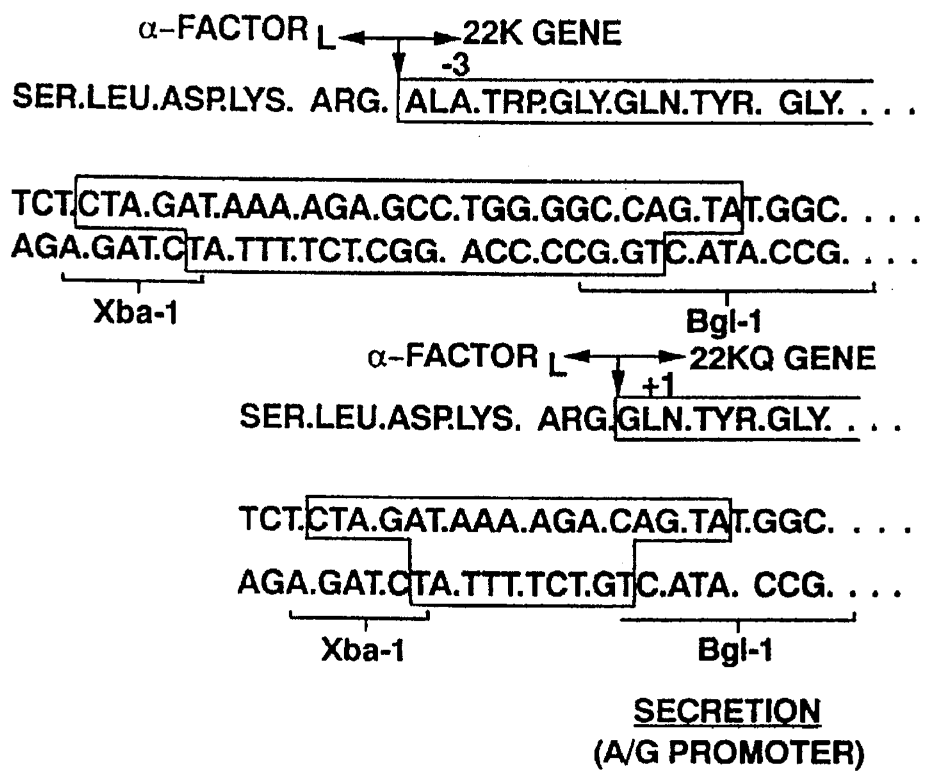
FIG. 4B illustrates oligonucleotide adapters (boxed) used to prepare BCF expression vectors which are secreted from yeast using the alpha-factor signal peptide.

Yeast expression vectors were constructed for intracellular production or secretion of hBCF from the ADH2/GAPDH regulatable promoter. Since the first cDNA clone did not contain DNA encoding a signal peptide, methionine-4, was used as the N-terminal amino acid for these constructions. Subsequent cDNA analyses, and identification of a classical signal peptide, and a signal peptidase cleavage site, allowed construction of a yeast α-factor/hBCF fusion with glutamine +1 as the N-terminal amino acid of recombinant hBCF. For cloning into expression vectors, natural Nco-1, Bgl-1 and Spe-1 sites were used together with the synthetic oligonucleotide adapters shown (FIG. 4B). Since Spe-1 and Xba-1 give the same restriction enzyme overhang, the initial construction was simply an insertion of the Nco-1/SPE-1 hBCF gene into Nco-1/Xba-1 digested pBS100haFGF, a vector containing ADH2/GAPDH promoter and GAPDH terminator elements flanking a synthetic human acidic fibroblast growth factor (FGF) gene. The haFGF gene contains an Nco-1 and unique Xba-1 sites. The resulting plasmid, pBS100hBCF, was used for further constructions. Thus, the Nco-1/Sal-1 fragment containing the hBCF gene was cloned together with BAMH1/Nco-1 fragments encoding the GAPDH and ADH2/GAPDH promoters into BamH1/Sal-1 digested pBS24.1. The resulting plasmids, pBS24A/GhBCFKQ (−4 to 183) and pBS24 GAPhBCF (−3 to 183), were used to direct intracellular expression of hBCF. For secretion, Bgl-1/Sal-1 fragments were excised and cloned into pBS24.1 together with BamH1/Xba-1 fragments encoding the ADH2/GAPDH promoter, the yeast α-factor secretory signal/leader sequence, and the synthetic linkers shown in FIG. 4B (boxed), for expression of hBCF(−4 to 183) and hBCF (1–183). Yeast cells transformed with expression plasmids encoding ADH2/GAPDH promoter-hBCF(-4-183) and GAPDH promoter-hBCF(-4–183) fusions, as analyzed by SDS-PAGE and Coomassie blue staining of total proteins, showed no expression as compared with control yeast cells. Therefore, to study secretion systems, the pBS24 plasmids containing α-factor leader-hBCF (−3–183) and hBCF (1–183) fusions were constructed. In each case, transcription was driven by the ADH2/GAPDH promoter. Yeast strain AB110 was transformed with the yeast expression plasmids, and yeast supernatants were analyzed by precipitation with 10% trichloroacetic acid and separation by SDS-PAGE. High levels of expression of the approximately 22 kD product was observed by Coomassie blue staining, when compared with control yeast cells transformed with the parent yeast vector pBS24. The transformant AB110 (pBS24.1 22 kQ) is deposited under accession number ATCC 20948. The active lot of yeast cells comprised a pool of two lots, KQ-2 and KQ-3, from which the recombinant BCF was isolated and purified as follows.

Lot KQ-2

The cells were removed by centrifugation from the fermentation medium, and the medium concentrated using a YM10 Amicon spiral cartridge. The concentrate was diafiltered into water, then 20 mM Tris-Cl, 1 mM EDTA, 3 M NaCl, pH 7.5. This was passed over a column of prep grade Superose 12 at 4° C., then at room temperature. The 22KBCF did not stick to either column. The flowthrough was purified by adsorption onto Superose 12 HR 10/30, and eluted with the same buffer but with 1 M NaCl.

Lot KQ-3

The cells were removed and the medium concentrated as described above. The concentrate was diafiltered against water, then 20 mM Tris-Cl, 1 mM EDTA, pH 7.5. This was loaded onto a Mono-Q HR 10/10 column, washed, and eluted with a gradient to 0.5 M NaCl. The 22KBCF-containing fractions were identified by gel electrophoresis, pooled, adjusted to 3 M NaCl with solid NaCl, and loaded onto a Superose 12 HR 10/30 column. The 22KBCF was eluted with buffer containing 1 M NaCl.

Lot KQ-2/3

The Superose eluates (from Lots KQ-2 and KQ-3) were pooled, concentrated using YM 10 membrane in Amicon stirred cell, dialyzed versus water, and lyophilized.

Alternatively, the recombinant BCF may be isolated and purified as follows.

The media is removed from the cells and concentrated approximately ten fold. The pH is adjusted to 7.5, the concentrate is diluted to a conductivity below 5 mS/cm, then applied to Fast Flow Q ion-exchange resin pre-equilibrated with 50 mM Tris/Hcl, 1 mM EDTA, 1 mM PMSF, pH 7.5. The column is washed with 1 column volume of the above buffer and eluted using a 0–1 M NaCl salt gradient in the above buffer. The 22KBCF is eluted at a conductivity of 20–30 mS/cm, which is confirmed using SDS-PAGE. The 22KBCF containing fractions are pooled, the pH maintained at 7.5 and made 4M with respect to Urea, concentrated, and run over a S-100 sizing column in 4M Urea, 100 mM Tris/HCl, 1 mM EDTA, 1 mM PMSF at pH 7.5. The 22KBCF containing fractions are identified by SDS-PAGE, pooled, concentrated, and dialysed against 10 mM ammonium bicarbonate pH 7.8. The 22KBCF is then lyophilized and may be stored dry at 4° C.

EXAMPLE 7

A sample of purified recombinant human BCF(rhBCF) expressed as in Example 6, 1 mg (lot KQ 2/3), was dissolved in water containing 5 mg of human fibrin. The rBCF-fibrin composite was lyophilized and implanted in the mouse thigh muscle pouch. In another mouse, bovine matrix Gla protein was dissolved in 6M urea containing 1 mg of human rhBCF and dialyzed against water. The precipitate and supernatant were lyophilized to prepare a composite of MGP and hBCF proteins. The composite was implanted in the quadriceps pouch. For controls, the contralateral thighs were implanted with bovine matrix Gla protein plus albumin in one mouse; in the other mouse the control consisted of 5 mg of human fibrin and 1.0 mg of albumin.

Figure 5:
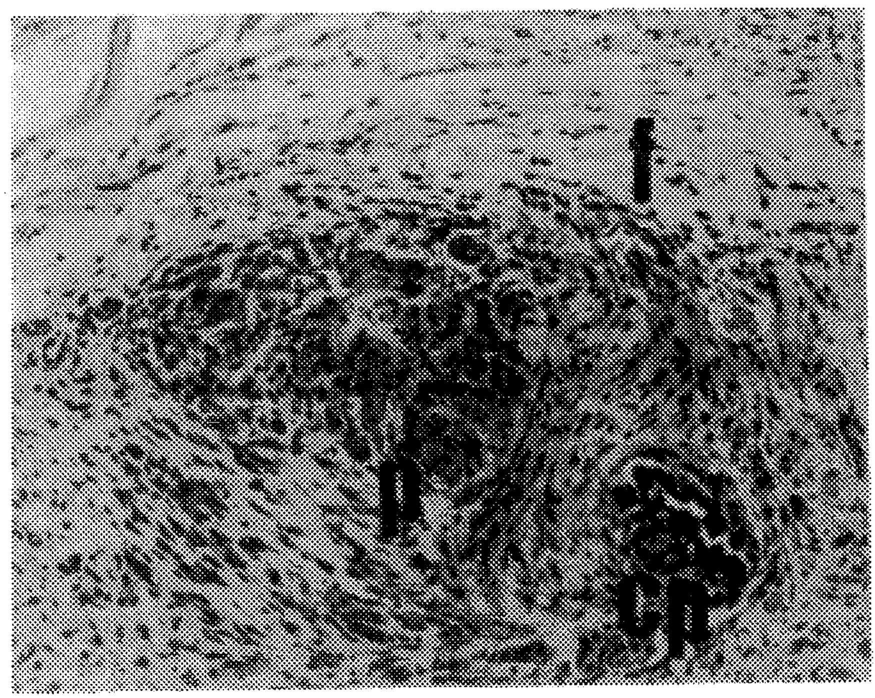
FIGS. 5, 6 and 7 are photomicrographs of the quadriceps pouches of mice 21 days after implantation of a composite of recombinant hBCF and MGP, showing initiation of calcification.
Figure 6:
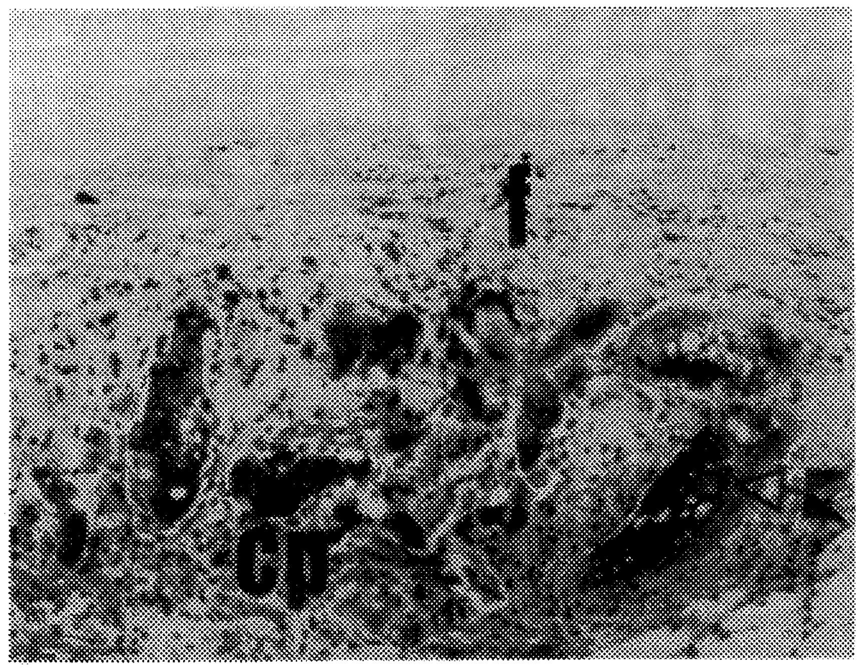

Microradiographs of the rBCF-matrix Gla protein composite showed areas of calcified tissue. Histological sections showed small round cells, multinucleated cells, macrophages with hyperplasia and hypertrophy of mesenchymal type cells. There were plates of calcified ground substance but no cartilage or bone cells. FIG. 5 is a photomicrograph showing hyperplasia and hypertrophy of connective tissue cells on the surface of a composite implant (indicated by P) of recombinant protein hBCF (Lot KQ 2/3, 1 mg) and 1 mg of human matrix Gla protein. Calcification of the implanted proteins is indicated by CP in the quadriceps pouch of a mouse on day 21. The fibrous connective tissue envelope is indicated by F. FIG. 6 is a photomicrograph showing islands of calcified protein (CP) induced by a composite of recombinant hBCF and biological human matrix Gla protein. Note the large foam cell (arrow). The entire implant is enclosed in a fibrous capsule (F) by day 21.

Figure 7:
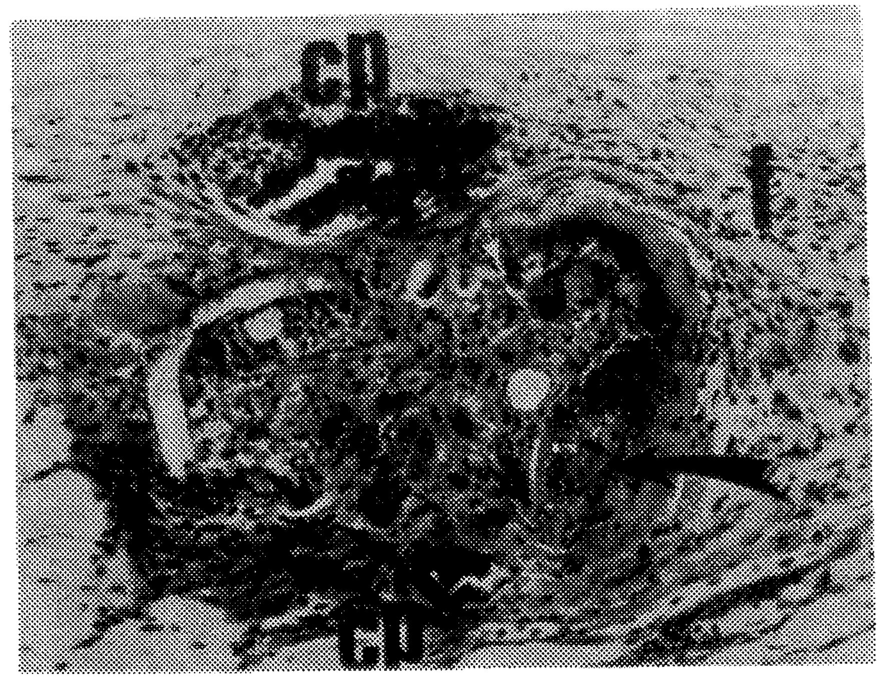

FIG. 7 is a photomicrograph showing a composite of recombinant hBCF and matrix Gla protein on day 21. Note the highly vascular interior of the implant including small round cells, multinucleated cells, macrophages, calcifying intercellular substance (CP) and large foam cells (arrow). All of the implanted protein and reactive tissue was enclosed in a fibrous envelope (F) on day 21.

We claim:

1. An isolated DNA fragment comprising the nucleotide sequence substantially as shown in FIG. 1E.

2. An isolated DNA fragment comprising the nucleotide sequence substantially as shown in FIG. 1F.

3. A recombinant DNA molecule comprising the following elements operably linked in the 5' to 3' direction:

a sequence comprising ATG GAC CTC AGT CTT CTC TGG GTA CTT CTG CCC CTA GTC ACC ATG GCC TGG GGC which encodes a hydrophobic peptide; and the DNA fragment of claim 1.

4. A recombinant DNA molecule comprising the following elements operably linked in the 5' to 3' direction:

a sequence comprising ATG GAC CTC ACT CTT CTG TGG GTG CTT CTG CCA CTG GTC ACC GTG GCT TGG GGA which encodes a hydrophobic peptide; and the DNA fragment of claim 2.

5. A method for producing a recombinant polypeptide that comprises an amino acid sequence as shown in FIG. 1C, comprising the steps of:

(a) constructing a vector that comprises the DNA fragment according to claim 8, (b) transforming a host cell with said vector, and (c) culturine the resultant transformed cell under conditions to express the peptide encoded by said DNA fragment.

6. A method for producing a recombinant polypeptide that comprises an amino acid sequence as shown in FIG. 1D, comprising the steps of:

(a) constructing a vector that comprises the DNA fragment according to claim 2, (b) transforming a host cell with said vector, and (c) culturing the resultant transformed cell under conditions to express the peptide encoded by said DNA fragment.

7. A method according to claim 5 wherein said DNA fragment is operably linked at its 5' end to a sequence comprising ATG GAG CTC ACT CTT CTC TGG GTA CTT CTG CCC CTA GTC ACC ATG GCC TGG GGC which encodes a hydrophobic peptide.

8. A method according to claim 6 wherein said DNA fragment is operably linked at its 5' end to a sequence comprising ATG GAC CTC ACT CTT CTG TGG GTG CTT CTG CCA CTG GTC ACC GTG GCT TGG GGA which encodes a hydrophobic peptide.

9. A method according to any one of claims 5 through 8 wherein said host cell is eukaryotic.

10. A method according to claim 9, wherein said host cell is a yeast cell.

11. A method according to claim 10 wherein said vector comprises a GAPDH promoter which controls expression of said peptide.

12. A method according to claim 10 wherein said promoter comprises an ADH2/GAPDH promoter which controls expression of said peptide.

13. A replicable vector comprising DNA according to claim 1.

14. A replicable vector comprising DNA according to claim 2.

15. A replicable vector comprising DNA according to claim 3.

16. A replicable vector comprising DNA according to claim 4.

17. A host cell transformed with a replicable vector according to claim 13.

18. A host cell transformed with a replicable vector according to claim 14.

19. A host cell transformed with a replicable vector according to claim 15.

20. A host cell transformed with a replicable vector according to claim 16.

21. An isolated DNA molecule comprising the nucleotide sequence substantially as shown in FIG. 1A and 1B or a fragment thereof, wherein said fragment is at least about 18 bases in length.

22. The isolated DNA molecule of claim 21 comprising the nucleotide sequence substantially as shown in FIG. 1A and 1B or a fragment thereof, wherein said fragment is at least 18 bases in length.

23. The isolated DNA molecule of claim 21 comprising the nucleotide sequence substantially as shown in FIG. 1A and 1B or a fragment thereof, wherein said fragment is 18 bases in length.

24. The DNA fragment according to claim 21, wherein the fragment is either form of Probe A of FIG. 2.

* * * * *